United States Patent [19]

Klaus et al.

[11] Patent Number: 4,816,476
[45] Date of Patent: Mar. 28, 1989

[54] HETEROCYCLIC RODENTICIDAL COMPOUNDS, COMPOSITIONS CONTAINING THE COMPOUNDS, AND METHODS OF USE

[75] Inventors: Michael Klaus, Weil am Rhein, Fed. Rep. of Germany; Peter Loeliger, Muttenz; Harald Weiser, Hochwald, both of Switzerland

[73] Assignee: Hoffmann-La Roche Inc., Nutley, N.J.

[21] Appl. No.: 940,994

[22] Filed: Dec. 12, 1986

Related U.S. Application Data

[62] Division of Ser. No. 725,181, Apr. 19, 1985, Pat. No. 4,659,735, which is a division of Ser. No. 507,857, Jun. 27, 1983, Pat. No. 4,535,086.

[30] Foreign Application Priority Data

Jul. 6, 1982 [CH] Switzerland .................. 4117/82
May 19, 1983 [CH] Switzerland .................. 2728/83

[51] Int. Cl.$^4$ .................. C07D 333/56; A61K 31/38
[52] U.S. Cl. .................. 514/443; 514/469; 549/58; 549/471
[58] Field of Search .................. 549/471, 58; 514/469, 514/443

[56] References Cited

U.S. PATENT DOCUMENTS

| | | | |
|---|---|---|---|
| 3,872,114 | 3/1975 | Sahm et al. | 549/437 |
| 4,193,931 | 3/1980 | Loeliger | 514/510 |
| 4,326,055 | 4/1982 | Loeliger | 548/237 |

*Primary Examiner*—Jane T. Fan
*Attorney, Agent, or Firm*—Jon S. Saxe; Bernard S. Leon; Richard J. Mazza

[57] ABSTRACT

Heterocyclic compounds of the formula

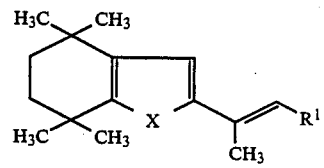

wherein X is —CH=CH—, —O— or —S—; $R^1$ is a group Ar—$R^2$ or —CH=CH—C(CH$_3$)=CH—$R^{21}$; Ar is phenyl, pyridyl, furyl or thienyl; $R^2$ is a group —CO$_2R^3$, —C(O)$R^4$, —CH$_2$O$R^3$, lower-alkylsulphonyl or formyl; $R^{21}$ is a group —CO$_2R^3$, —C(O)$R^4$, —CH$_2$O$R^3$ or formyl; $R^3$ is hydrogen or lower-alkyl and $R^4$ is hydrogen, hydroxy, amino, lower alkylamino, di-(lower alkyl)amino or lower-alkyl; at least one ring of the molecule being heterocyclic, salts thereof, processes for their preparation, rodenticidal compositions containing these compounds as the active ingredient and methods of use of the rodenticidal compositions are disclosed.

6 Claims, No Drawings

HETEROCYCLIC RODENTICIDAL COMPOUNDS, COMPOSITIONS CONTAINING THE COMPOUNDS, AND METHODS OF USE

This is a division, of application Ser. No. 725,181 filed Apr. 19, 1985, now U.S. Pat. No. 4,659,735 which is a divisional of Ser. No. 507,857, filed June 27, 1983, now U.S. Pat. No. 4,535,086.

SUMMARY OF THE INVENTION

This invention relates to heterocyclic compounds of the formula

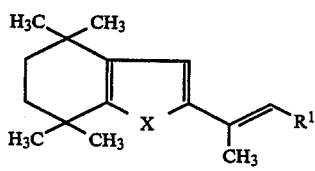

wherein X is —CH=CH—, —O— or —S—; $R^1$ is a group Ar—$R^2$ or —CH=CH—C($CH_3$)=CH—$R^{21}$; Ar is phenyl, pyridyl, furyl or thienyl; $R^2$ is a group —$CO_2R^3$, —C(O)$R^4$, —$CH_2OR^3$, lower-alkylsulphonyl or formyl; $R^{21}$ is a group —$CO_2R^3$, —C(O)$R^4$, —$CH_2OR^3$ or formyl; $R^3$ is hydrogen or lower-alkyl and $R^4$ is hydrogen, hydroxy, amino, lower alkylamino, di-(lower alkyl)amino or lower-alkyl; at least one ring of the molecule being heterocyclic, and salts thereof. This invention is also directed to rodenticidal compositions containing, as the active ingredient, a compound of formula I and methods for the use of these rodenticidal compositions.

DETAILED DESCRIPTION OF THE INVENTION

The invention is directed to heterocyclic compounds of the formula

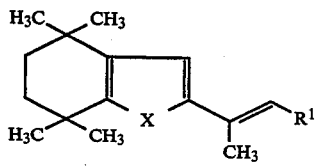

wherein X is —CH=CH—, —O— or —S—; $R^1$ is a group Ar—$R^2$ or —CH=CH—C($CH_3$)=CH—$R^{21}$; Ar is phenyl, pyridyl, furyl or thienyl; $R^2$ is a group —$CO_2R^3$, —C(O)$R^4$, —$CH_2OR^3$, lower-alkylsulphonyl or formyl; $R^{21}$ is a group —$CO_2R^3$, —C(O)$R^4$, —$CH_2OR^3$ or formyl; $R^3$ is hydrogen or lower-alkyl and $R^4$ is hydrogen, hydroxy, amino, lower alkylamino, di-(lower alkyl)amino or lower-alkyl; at least one ring of the molecule being heterocyclic, and salts thereof.

The invention is also directed to processes for the preparation of the compounds of formula I and salts thereof as well as rodenticidal compositions which contain a compound of formula I or a salt thereof.

The term lower-alkyl used herein encompasses both straight- and branched-alkyl groups containing 1 to 6, preferably 1 to 4, carbon atoms, such as methyl, ethyl, propyl, isopropyl, butyl and sec.butyl. Preferred alkyl groups are methyl and ethyl.

Preferred compounds of formula I are those in which X is —S— or —O— and $R^1$ is a group Ar—$R^2$ wherein Ar is phenyl or pyridyl and $R^2$ is lower-alkoxycarbonyl.

Particularly preferred compounds of formula I are ethyl p-[2-(4,5,6,7-tetrahydro-4,4,7,7-tetramethylbenzo[b]thien-yl)propenyl)benzoate and ethyl p-[2-(4,5,6,7-tetrahydro-4,4,7,7-tetramethyl-2-benzofuranyl)propenyl]benzoate.

The compounds of formula I and salts thereof are prepared by one of the procedures described below.

A. Reacting a compound of the phosphonium salt of the formula

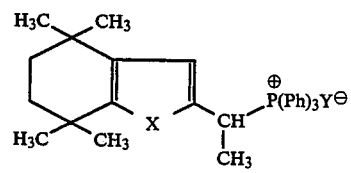

with a formyl compound of the formula

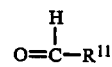

wherein in formulae II–III Ph represents phenyl; and $R^{11}$ represents a group —Ar$CO_2R^3$, —Ar$SO_2$-lower-alkyl or —CH=CH—C($CH_3$)=CH$CO_2R^3$ and $R^1$, $R^3$, Ar and X are as defined previously; and $Y^\ominus$ is the anion of an inorganic or organic acid.

The chloride, bromide or hydrosulphate ion is the preferred inorganic acid anion denoted by $Y^\ominus$ and the tosyloxy ion is the preferred organic acid anion denoted by $Y^\ominus$.

The reaction of a formyl compound of formula III with a phosphonium salt of formula II is carried out in a manner known in the art in the presence of an acid-binding agent. Suitable acid-binding agents include a strong base, such as, for example, butyl lithium, sodium hydride or a sodium salt of dimethyl sulphoxide. The reaction is conveniently carried out in a solvent, for example, in an ether, such as diethyl ether or tetrahydrofuran, or in an aromatic hydrocarbon, such as benzene. The temperature of the reaction varies between room temperature and the boiling point of the reaction mixture.

B. Reacting a compound of the formula

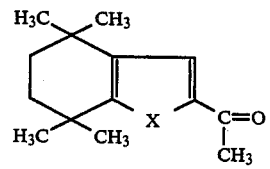

with a phosphonate compound of the formula

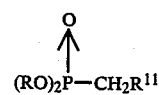

wherein in formulae IV–V R represents lower-alkoxy; and $R^{11}$ represents a group —Ar$CO_2R^3$, —Ar$SO_2$-loweralkyl or —CH=CH—C($CH_3$)=CH$CO_2R^3$ and $R^1$, $R^3$, Ar and X are as defined previously.

The reaction of a phosphonate of formula V with a compound of formula IV is also carried out in a manner known in the art in the presence of a base and, preferably, in the presence of an inert organic solvent. The reaction can be carried out in the presence of sodium hydride in benzene, toluene, dimethylformamide, tetrahydrofuran, dioxan or 1,2-dimethoxyethane, or in the presence of a sodium alcoholate in an alkanol, for example, sodium methylate in methanol. The reaction is carried out at a temperature between 0° C. and the boiling point of the reaction mixture.

If desired, the carboxylic acid esters of formula I obtained by the above procedures can be transformed to other derivatives. For example, the carboxylic acid ester can be converted to the corresponding amide; the ester can be hydrolyzed to the carboxylic acid which can be transformed into a salt. The carboxylic acid can also be reduced to the alcohol and, if desired, the alcohol can be etherified or oxidized to the formyl compound.

A carboxylic acid ester of formula I can be hydrolyzed by methods known per se to the carboxylic acid. For example, the ester can be treated with alkali, especially by treatment with aqueous alcoholic sodium or potassium hydroxide solution at a temperature between room temperature and the boiling point of the reaction mixture. The resulting carboxylic acid can be amidated either via an acid halide or directly, as described hereinafter.

A carboxylic acid of formula I can be converted by methods known per se to the acid chloride. For example, the acid can be treated with thionyl chloride, preferably in pyridine, or phosphorous trichloride in toluene. The acid chloride can be converted into an ester by reaction with an alcohol or into a corresponding amide by reaction with an amine.

A carboxylic acid ester of formula I can be converted directly into the corresponding amide, for example, by treatment with lithium amide. The lithium amide is advantageously reacted at room temperature with the ester in question.

A carboxylic acid or carboxylic acid ester of formula I can be reduced by methods known per se to give the corresponding alcohol of formula I. The reduction is advantageously carried out with the aid of a metal hydride or alkyl metal hydride in an inert solvent. Especially suitable hydrides are mixed metal hydrides such as lithium aluminium hydride or bis-[methoxy-ethyleneoxy]-sodium aluminium hydride. Suitable solvents are, inter alia, ether, tetrahydrofuran or dioxan when lithium aluminium hydride is used and ether, hexane, benzene or toluene when diisobutylaluminium hydride or bis-[methoxy-ethyleneoxy]-sodium aluminium hydride is used.

An alcohol of formula I ($R^2 = CH_2OH$) can be etherified with an alkyl halide, for example, with ethyl iodide, in the presence of a base, preferably in the presence of sodium hydride, in an organic solvent such as dioxan, tetrahydrofuran, 1,2-dimethoxyethane or dimethylformamide. The ether can also be formed by reacting the alcohol of formula I in the presence of an alkali metal alcoholate in an alkanol at a temperature between 0° C. and room temperature.

An alcohol of formula I can be oxidized to the corresponding formyl compound ($R^2 = CHO$) by methods known per se by treatment with an oxidizing agent such as manganese dioxide in an inert solvent, for example, methylene chloride, hexane or tetrahydrofuran. The oxidation is conveniently carried out at room temperature. The oxidation can also be carried out, for example, using pyridinium chlorochromate as the oxidizing agent or according to the Pfitzner-Moffat or the Oppenauer procedure.

A carboxylic acid of formula I forms salts with bases, especially with the alkali metal hydroxides and preferably with sodium hydroxide or potassium hydroxide.

Preparation of the compounds of formula I can result in mixtures of cis and trans isomers. If desired, the mixture can be separated by methods known per se into the cis and trans components or isomerized to the all trans isomer.

This invention is also directed to rodenticidal compositions which comprise inert carrier material and, as the active ingredient, a compound of formula I. The compositions are used in liquid or solid baits. The inert carrier materials which are useful in preparing the compositions of this invention are all those which are conventional in formulating rodenticidal compositions. Examples of carrier substances are nutrients, such as sugar and sugar-containing substances, starch, cereals, gelatine and fats; mineral substances, such as calcium silicate, calcium carbonate, calcium phosphate and silica; preserving agents, such as chlorinated phenols; hydrophobic agents, such as natural and synthetic waxes; colorants; moisture-retaining agents, such as polyglycols, neutralizing agents, such as alkanolamines.

The compounds of formula I and salts thereof can also be present in the form of solid or liquid concentrates, master mixes, which can be converted into baits using suitable extenders and/or feedstuffs, for example, wheat, maize, carob beans, bananas, peanuts. The baits conveniently contain the compounds of formula I or salts thereof in amounts of about 0.1 to 100 ppm, preferably 50–100 ppm.

The compounds of formula I and their salts can be used as rodenticides. In rats they show even in small dosages a powerful toxic effect which, however, is recognizable only several days after the intoxication. For example, the oral administration of ethyl p-[2-(4,5,6,7-tetrahydro-4,4,7,7-tetramethylbenzo[b]thien-2-yl)propenyl]benzoate to rats in dosages of 1.25 mg/kg led to the death of all animals within 8 days, although no animal died in the first 5 days.

The following Examples illustrate the invention:

EXAMPLE 1

30 g of [1-(4,5,6,7-tetrahydro-4,4,7,7-tetramethylbenzo[b]thien-2-yl)ethyl]triphenylphosphonium bromide and 9.5 g of 4-ethoxycarbonylbenzaldehyde are suspended in 300 ml of butylene oxide and the mixture is heated at reflux for 4 hours. The thus-obtained solution is concentrated to one third of the original volume in a water-jet vacuum, poured into 500 ml of a methanol/water mixture (6:4) and extracted several times with hexane. The organic phase is washed three times with water, dried over sodium sulphate and evaporated. There is obtained a light brownish oil which is purified by filtration over silica gel (eluting agent hexane/ether 19:1). After recrystallization from hexane, there are obtained 11.3 g of ethyl p-[2-(4,5,6,7-tetrahydro-4,4,7,7-tetramethylbenzo[b]thien-2-yl)propenyl]benzoate in the form of colorless crystals, m.p. 118°–120° C.

The [1-(4,5,6,7-tetrahydro-4,4,7,7-tetramethylbenzo[b]thien-2-yl)ethyl]triphenylphosphonium bromide used as the starting material can be prepared as follows:

90 g of 2,5-dimethyl-2,5-dichlorohexane and 195 ml of thiophene are dissolved in 400 ml of hexane. 54 ml of titanium tetrachloride are slowly added dropwise thereto while cooling with ice, the mixture is warmed to 40° C. for 1.5 hours, again cooled with ice and the dark red mixture is treated cautiously with ice-water. The mixture is extracted three times with ether, the organic phase is washed with saturated sodium bicarbonate solution, dried and evaporated. The thus-obtained black oil is firsly filtered over silica gel (eluting agent hexane) and subsequently distilled in a water-jet vacuum. There are obtained 18.5 g of 4,5,6,7-tetrahydro-4,4,7,7-tetramethylbenzo[b]thiophene as a colorless liquid, b.p. 95°–96° C./10 mm.

18.2 g of 4,5,6,7-tetrahydro-4,4,7,7-tetramethylbenzo[b]thiophene and 7.4 g of acetyl chloride are dissolved in 200 ml of benzene and the solution is cooled to 0° C. At this temperature there are slowly added dropwise thereto 24.4 g of tin tetrachloride. After stirring at room temperature for 2.5 hours, the mixture is again cooled to 0° C. and a mixture of 9.3 ml of concentrated hydrochloric acid and 36.4 ml of water is added dropwise thereto. The mixture is extracted with ether, the organic phase is washed once with water, dried, evaporated and distilled in a high vacuum. There are obtained 21.7 g of 2-acetyl-4,5,6,7-tetrahydro-4,4,7,7-tetramethylbenzo[b]thiophene as a colorless liquid, b.p. 108°–115° C./0.05 mm, which can be crystallized from hexane, m.p. 53°–55° C.

21.7 g of 2-acetyl-4,5,6,7-tetrahydro-4,4,7,7-tetramethylbenzo[b]thiophene are dissolved in 250 ml of ethanol and the solution is treated gradually with 5.5 g of sodium borohydride. The mixture is left to come to room temperature and is stirred for a further 2 hours. The mixture is poured on to ice, extracted with ether, the organic phase is washed once with saturated sodium chloride solution, dried and evaporated. The crude product is filtered over silica gel (eluting agent hexane/ether 3:1) and recrystallized from hexane. There are obtained 20.2 g of 4,5,6,7-tetrahydro-$\alpha$,4,4,7,7-pentamethylbenzo[b]thiophene-methanol in the form of colorless crystals, m.p. 53°–55° C.

20.2 g of 4,5,6,7-tetrahydro-$\alpha$,4,4,7,7-pentamethylbenzo[b]thiophene-methanol are dissolved in 260 ml of acetonitrile and the solution is treated with 29.2 g of triphenylphosphonium bromide. After stirring at 50° C. for 3 hours, the mixture is evaporated to dryness, the residue is taken up with 80% aqueous ethanol and extracted twice with hexane. The ethanol phase is evaporated, the residue is dissolved in methylene chloride, the solution is dried over sodium sulphate and evaporated. There are obtained 49.4 g of [1-(4,5,6,7-tetrahydro-4,4,7,7-tetramethylbenzo[b]thien-2-yl)ethyl]triphenylphosphonium bromide as an amorphous white powder.

EXAMPLE 2

4.50 g of [1-(4,5,6,7-tetrahydro-4,4,7,7-tetramethylbenzo[b]thien-2-yl)ethyl]ethyl]triphenylphosphonium bromide and 1.3 g of ethyl 5-formyl-3-methylpenta-2,4-dienoate are dissolved in 70 ml of butylene oxide and the solution is heated at refluxed for 2 hours. The cooled mixture is poured into a methanol/water mixture (6:4) and extracted several times with hexane. The hexane phase is washed three times with water, dried and evaporated. After filtration of the crude product over silica gel (eluting agent hexane/ether 9:1), there are obtained 24 g of ethyl 3-methyl-7-(4,5,6,7-tetrahydro-4,4,7,7-tetramethylbenzo[b]thien-2-yl)-2,4,6-octatrienoate as a pale yellowish oil.

2.4 g of the thus-obtained ethyl ester are dissolved in 40 ml of ethanol and the solution is treated with a solution of 2.5 g of potassium hydroxide in 10 ml of water. The mixture is warmed to 50° C. for 3 hours, poured into ice/water, acidified with 2N hydrochloric acid and extracted several times with ethyl acetate. The organic phase is washed with water, dried and evaporated. Recrystallization of the residue from ethyl acetate gives 1.5 g of 3-methyl-7-(4,5,6,7-tetrahydro-4,4,7,7-tetramethylbenzo[b]thien-2-yl)-2,4,6-octatrienoic acid as pale yellowish crystals, m.p. 226°–228° C.

EXAMPLE 3

In the manner described above, from 5.0 g of [1-(4,5,6,7-tetrahydro-4,4,7,7-tetramethylbenzo[b]thien-2-yl)ethyl]triphenylphosphonium bromide and 1.65 g of ethyl 5-formyl-thiophene-2-carboxylate there are obtained, after recrystallization from hexane, 2.5 g of ethyl 5-[2-(4,5,6,7-tetrahydro-4,4,7,7-tetramethylbenzo[b]thien-2-yl)propenyl]-2-thiophenecarboxylate in the form of yellow crystals, m.p. 125°–127° C.

EXAMPLE 4

In the same manner, from 8.0 g of [1-(4,5,6,7-tetrahydro-4,4,7,7-tetramethylbenzo[b]thien-2-yl)ethyl]triphenylphosphonium bromide and 2.4 g of ethyl 5-formyl-furan-2-carboxylate there are obtained, after recrystallization from hexane, 2.9 g of ethyl 5[(2-(4,5,6,7-tetrahydro-4,4,7,7-tetramethylbenzo[b]thien-2-yl)propenyl]-2-furancarboxylate as pale yellow crystals, m.p. 78°–82° C.

EXAMPLE 5

In the same manner, from 10 g of [1-(4,5,6,7-tetrahydro-4,4,7,7-tetramethylbenzo[b]thien-2-yl)ethyl]triphenylphosphonium bromide and 3.5 g of 4-ethylsulphonylbenzaldehyde there are obtained, after recrystallization from hexane/ethyl acetate, 4.5 g of 2-[2-[p-(ethylsulphonyl)phenyl]-1-methylvinyl]-4,5,6,7-tetrahydro-4,4,7,7-tetramethylbenzo[b]thiophene as pale yellow crystals, m.p. 148°–150° C.

EXAMPLE 6

In the same manner, from 3.9 g of [1-(5,6,7,8-tetrahydro-5,5,8,8-tetramethyl-2-naphthyl)ethyl]triphenylphosphonium bromide and 1.3 g of ethyl 5-formyl-thiophene-2-carboxylate there are obtained, after recrystallization from hexane, 1.8 g of ethyl 5-[(E)-2-(5,6,7,8-tetrahydro-5,5,8,8-tetramethyl-2-naphthyl)propenyl]-2-thiophenecarboxylate as colorless crystals, m.p. 110°–111° C.

EXAMPLE 7

In the same manner, from 2.9 g of [1-(5,6,7,8-tetrahydro-5,5,8,8-tetramethyl-2-naphthyl)ethyl]triphenyl phosphonium bromide and 0.9 g of ethyl 5-formyl-furan-2-carboxylate there is obtained, after recrystallization from hexane, 0.9 g of ethyl 5-[2-(5,6,7,8-tetrahydro-5,5,8,8-tetramethyl-2-naphthyl)propenyl]-2-furancarboxylate as pale yellow crystals, m.p. 114°–115° C.

EXAMPLE 8

In the same manner, from 5.6 g of [1-(5,6,7,8-tetrahydro-5,5,8,8-tetramethyl-2-naphthyl)ethyl]triphenyl phosphonium bromide and 1.4 g of ethyl 6-formyl-pyridine-3-carboxylate there is obtained, after chromatography on silica gel (eluting agent hexane/ether 2:1) and crystallization from hexane, 0.6 g of ethyl 6-[(E)-2-(5,6,7,8-tetrahydro-5,5,8,8-tetramethyl-2-naphthyl)-propenyl]nicotinate in the form of colorless crystals, m.p. 114°–115° C.

EXAMPLE 9

In the same manner, from 4.6 g of [1-(4,5,6,7-tetrahydro-4,4,7,7-tetramethylbenzo[b]furan-2-yl)ethyl]triphenylphosphonium bromide and 1.5 g of 4-ethoxycarbonylbenzaldehyde there are obtained, after chromatography on silica gel (eluting agent hexane/ether 9:1) and crystallization from hexane, 2.2 g of ethyl p-[2-(4,5,6,7-tetrahydro-4,4,7,7-tetramethyl-2-benzofuranyl)propenyl]benzoate in the form of colorless crystals, m.p. 96.97° C.

The [1-(4,5,6,7-tetrahydro-4,4,7,7-tetramethylbenzo[b]furan-2-yl)ethyl]triphenylphosphonium bromide used as the starting material can be prepared as follows:

5.2 g of magnesium shavings are suspended in 100 ml of absolute ether and treated dropwise with 13.5 ml of methyl iodide. After the addition of 100 ml of ether, the mixture is boiled at reflux for a further 3 hours until all magnesium has dissolved. The mixture is cooled to 0° C. and treated with 20.7 g of finely powdered copper (I) iodide. After stirring at 0° C. for 15 minutes, a solution of 10 g of 3,6,6-trimethyl-2-cyclohexanone in 40 ml of ether is added dropwise thereto and the mixture is stirred at 0° C. for a further 4 hours. Thereafter, the yellow suspension is poured into ice/2N hydrochloric acid, extracted several times with ether, the organic phase is dried and evaporated. The residue is distilled in a water-jet vacuum. There are obtained 9 g of 2,2,5,5-tetramethylcyclohexanone as a colorless liquid, b.p. 71°-74° C./15 mm.

A solution of 26.4 g of 2,2,5,5-tetramethylcyclohexanone in 250 ml of ether is added dropwise at −20° C. to 102.8 ml of methyl lithium (2 molar in ether). After stirring at 0° C. for 2.5 hours, the mixture is poured into ice/1N hydrochloric acid and extracted with ether. The organic phase is washed with water, dried and evaporated. The residue is distilled in a water-jet vacuum. There are obtained 22.6 g of 1,2,2,5,5-pentamethylcyclohexanol as a colorless liquid, b.p. 81°-87° C./17 mm.

22.6 g of 1,2,2,5,5-pentamethylcyclohexanol are dissolved in 280 ml of benzene and, after the addition of 100 mg of p-toluenesulphonic acid, the mixture is boiled on a water separator for 7 hours. After cooling the solution, some solid sodium carbonate is added thereto, the mixture is filtered and the filtrate is evaporated at normal pressure. The residue is distilled in a water-jet vacuum. There are obtained 15.8 g of 1,3,3,6,6-pentamethylcyclohexen as a colorless liquid, b.p. 56°-57° C./17 mm.

15 g of 1,3,3,6,6-pentamethylcyclohexen are dissolved in 350 ml of carbon tetrachloride and the solution is treated with 19.3 g of N-bromosuccinimide. After the addition of a spatula tip of α,α'-azoisobutyronitrile, the mixture is boiled at reflux for 1.5 hours. The mixture is cooled, the resulting succinimide is filtered off and the filtrate is evaporated. There are obtained 23.8 g of a pale yellow oil which is processed immediately. The oil is dissolved in 350 ml of dimethylformamide and the solution is treated with 21 g of sodium benzenesulphinate. After stirring at room temperature for 72 hours, 600 ml of ether are added thereto, the mixture is left to stir for 15 minutes, the precipitated sodium bromide is filtered off and the filtrate is evaporated. The residue is taken up in water and extracted with ethyl acetate. After drying, evaporation and recrystallization from ether/hexane, there are obtained 22.2 g of phenyl (3,3,6,6-tetramethyl-1-cyclohexen-1-yl)methyl sulphone in the form of white crystals, m.p. 48°-50° C.

21.6 g of phenyl(3,3,6,6-tetramethyl-1-cyclohexen-1-yl)methyl sulphone are dissolved in 600 ml of tetrahydrofuran. At −40° C. there are added dropwise thereto 41.5 ml of butyl lithium (2 molar in hexane) and the mixture is stirred at −40° C. for a further 40 minutes. The orange solution is poured rapidly into a mixture of solid carbon dioxide and ether. After stirring for 30 minutes, the mixture is treated with water, acidified with 1N sulphuric acid and extracted with ethyl acetate. After drying, evaporation and recrystallization from ether/hexane, there are obtained 19.9 g of 3,3,6,6-tetramethyl-α-(phenylsulphonyl)-1-cyclohexane-1-acetic acid in the form of colorless crystals, m.p. 169°-174° C.

20.6 g of 3,3,6,6-tetramethyl-α-(phenylsulphonyl)-1-cyclohexen-1-acetic acid are dissolved in 800 ml of ethanol and the solution is treated at 0° C. with 107.1 g of sodium amalgam (5%). The mixture is stirred at room temperature for 4.5 hours, the solution is decanted off from the mercury, acidified with 2N hydrochloric acid and extracted with ethyl acetate. The organic phase is washed with water, dried, evaporated and filtered over silica gel (eluting agent hexane/ether 1:1). After recrystallization from hexane, there are obtained 10.2 g of 3,3,6,6-tetramethyl-1-cyclohexen-1-acetic acid in the form of colorless crystals, m.p. 50°-54° C.

10.2 g of 3,3,6,6-tetramethyl-1-cyclohexane-1-acetic acid are dissolved in 140 ml of methylene chloride and a solution of 14.2 g of thallium (I) ethylate in 80 ml of methylene chloride is added thereto at room temperature. The milky-white solution is now cooled to 0° C. and a solution of 2.7 ml of bromine in 70 ml of methylene chloride is slowly added dropwise thereto. After stirring at room temperature for 4 hours, the mixture is poured into ice/water and extracted with methylene chloride. The organic phase is washed with water, dried and evaporated. The thus-obtained crude product is filtered over silica gel (eluting agent hexane/ether 4:1). There are obtained 6.5 g of the corresponding lactone which is processed immediately. 6.5 g of the lactone are dissolved in 200 ml of methylene chloride and the solution treated dropwise at −70° C. with 40 ml of diisobutylaluminium hydride (20% in toluene). After stirring at −70° C. for 3.5 hours, 200 ml of a methanol/water mixture (1:1) are added dropwise thereto, the mixture is left to come to 0° C. and a further 100 ml of water are added dropwise thereto. The mixture is now acidified with 1N hydrochloric acid and extracted with ether. The organic phase is washed with water, dried and evaporated. After chromatography of the crude product on silica gel (eluting agent hexane/ether 9:1), there are obtained 4.8 g of 4,5,6,7-tetrahydro-4,4,7,7-tetramethylbenzo[b]furan as a colorless liquid.

1.6 g of 4,5,6,7-tetrahydro-4,4,7,7-tetramethylbenzo[b]furan are dissolved in 40 ml of tetrahydrofuran and the solution is treated dropwise at −30° C. with 5.2 ml of butyl lithium (2 normal in hexane). After stirring at −30° C. for 3.5 hours, a solution of 550 mg of acetaldehyde in 10 ml of tetrahydrofuran is added dropwise thereto. The mixture is left to come to room temperature, poured on to ice, extracted with ether, dried and evaporated. The thus-obtained pale yellowish oil (2.2 g) is dissolved in 35 ml of acetonitrile and the solution is treated with 3.8 g of triphenylphosphonium bromide. The mixture is warmed to 50° C. for 3 hours and subsequently evaporated to dryness. The oily residue is dissolved in 80% aqueous ethanol, the solution is extracted twice with hexane and the ethanol phase is evaporated to dryness. The residue is dissolved in methylene chloride, dried over sodium sulphate and evaporated. There are obtained 4.6 g of [1-(4,5,6,7-tetrahydro-4,4,7,7-tetramethylbenzo[b]furan-2-yl)ethyl]triphenylphosphonium bromide as a colorless amorphous substance.

EXAMPLE 10

3.0 g of ethyl p-[2-(4,5,6,7-tetrahydro-4,4,7,7-tetramethylbenzo[b]thien-2-yl)propenyl]benzoate are dissolved in 100 ml of ethanol and the solution is treated with a solution of 3.9 g of potassium hydroxide in 20 ml of water. After stirring at 50° C. for 3 hours, the mixture is cooled, poured into ice-water and acidified with 2N sulphuric acid. The mixture is extracted with ethyl acetate, the organic phase is washed with water, dried over sodium sulphate and evaporated. After recrystallization of the residue from ethyl acetate, there are obtained 2.4 g of p-[(E)-2-(4,5,6,7-tetrahydro-4,4,7,7-tetramethylbenzo[b]thien-2-yl)propenyl]benzoic acid in the form of pale yellowish crystals, m.p. 236°–238° C.

EXAMPLE 11

10.2 g of [1-(4,5,6,7-tetrahydro-4,4,7,7-tetramethylbenzo[b]thien-2-yl)ethyl]triphenylphosphonium bromide and 2.5 g of ethyl 6-formyl-pyridine-3-carboxylate are suspended in 100 ml of butylene oxide and heated at reflux for 1.5 hours. After working-up as described in Example 1, there are obtained 6.9 g of a yellow oil which is chromatographed over silica gel (eluting agent hexane/ether 9:1) in order to separate the undesired Z isomer. The E isomer which runs slower is recrystallized from hexane. There are obtained 1.3 g of ethyl 6-[(E)-2-(4,5,6,7-tetrahydro-4,4,7,7-tetramethylbenzo[b]thien-2-yl)propenyl]nicotinate in the form of yellowish crystals, m.p. 83°–84° C.

EXAMPLE 12

This Example illustrates the preparation of a rodenticidal composition of this invention. The following ingredients are mixed:

| Ingredient | Percent by Weight |
| --- | --- |
| A. Ethyl p-[2-(4,5,6,7-tetrahydro-4,4,7,7-tetramethylbenzo[b]thien-2-yl)propenyl]-benzoate | 0.005 |
| Preserving agent (chlorinated phenols) | 0.005 |
| Hydrophobic agent (natural and synthetic waxes) | 5.000 |
| Colouring agent (Berlin blue) | 0.300 |
| Bait (protein hydrolyzate) | 2.500 |
| Moisture-retaining agent (polyglycols) | 0.460 |
| Neutralizing agent (alkanolamines) | 0.060 |
| Inorganic carrier material (chalk) | 4.500 |
| Organic carrier material (wheat meal) | 86.675 |
| | 100.000 |
| B. Variable amounts of a compound of formula I | 0.005 |
| Maize meal | 65 |
| Rolled oats | 25 |
| Maize oil | 5 |
| Sugar ad | 5 |
| | 100 |

EXAMPLE 13

This Example illustrates the preparation of master mixes of this invention.

| Ingredient | Percent by Weight |
| --- | --- |
| A. Liquid master mix | |
| A compound of formula I | 0.25 |
| Oil (plant seed oil or mineral oil) | 99.75 |
| | 100.00 |
| B. Solid master mix | |
| A compound of formula I | 0.1 |
| Dust-preventing agent (mineral oil) | 10.0 |
| Inorganic carrier (kaolin) | 89.9 |
| | 100.0 |

These master mixes are mixed with various baits, for example, wheat, maize, carob beans, bananas, peanuts, etc., in an amount such that active ingredient concentrations of, for example, 0.005% are obtained.

We claim:

1. A compound of the formula

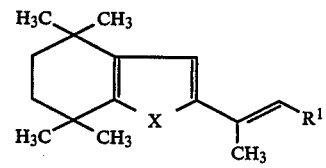

wherein X is —O— or —S—; $R^1$ is —CH═CH—C(CH$_3$)═CH—R$^{21}$; R$^{21}$ is a group —CO$_2$R$^3$, —C(O)R$^4$, —CH$_2$OR$^3$ or formyl; R$^3$ is hydrogen or lower-alkyl and R$^4$ is hydrogen, hydroxy, amino, lower-alkylamino, di-(lower-alkyl) amino or lower-alkyl; or a salt thereof.

2. The compound according to claim 1, 3-methyl-7-(4,5,6,7-tetrahydro-4,4,7,7-tetramethylbenzo[b]thien-2-yl)-2,4,6-octatrienoic acid.

3. A rodenticidal composition which comprises inert carrier material and, as the active ingredient, a rodentically effective amount of a compound of the formula

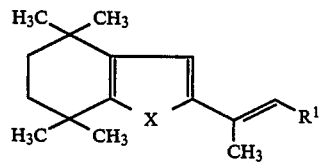

wherein X is —O— or —S—; $R^1$ is —CH═CH—C(CH$_3$)═CH—R$^{21}$; R$^{21}$ is a group —CO$_2$R$^3$, —C(O)R$^4$, —CH$_2$OR$^3$ or formyl; R$^3$ is hydrogen or lower-alkyl and R$^4$ is hydrogen, hydroxy, amino, lower-alkylamino, di-(lower-alkyl)amino or lower-alkyl; or a salt thereof.

4. A composition according to claim 3, in which the rodenticidally active compound is 3-methyl-7-(4,5,6,7-tetrahydro-4,4,7,7-tetramethylbenzo[b]thien-2-yl)-2,4,6-octatrienoic acid.

5. A method for eliminating rodents which comprises using an effective amount of a rodenticidal compound in a bait for said rodents, said compound being of the formula

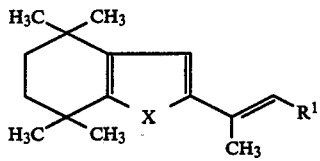
wherein X is —O— or —S—; R¹ is —CH=CH—C(CH₃)=CH—R²¹; R²¹ is a group —CO₂R³, —C(O)R⁴, —CH₂OR³ or formyl; R³ is hydrogen or lower-alkyl and R⁴ is hydrogen, hydroxy, amino, lower-alkylamino, di-(lower-alkyl)amino or lower alkyl; or a salt thereof.
6. A method according to claim 5, in which the rodentically active compound is 3-methyl-7-(4,5,6,7-tetrahydro-4,4,7,7-tetramethylbenzo[b]thien-2-yl)-2,4,6-octatrienoic acid.
* * * * *